United States Patent [19]

White

[11] 3,970,080

[45] July 20, 1976

[54] ANIMAL EAR SUPPORT DEVICE

[76] Inventor: Billy H. White, 2220 Garden St., Titusville, Fla. 32780

[22] Filed: Mar. 17, 1975

[21] Appl. No.: 559,033

[52] U.S. Cl. .......... 128/82; 119/96
[51] Int. Cl.² .......... A61F 13/00
[58] Field of Search .......... 128/82, 83, 89, 87, 128/152, 76; 119/96, 143, 108

[56] References Cited

UNITED STATES PATENTS

| | | | |
|---|---|---|---|
| 1,062,654 | 5/1913 | Lowman | 128/76 R |
| 2,070,403 | 2/1937 | Hershman | 128/152 |
| 2,587,966 | 3/1952 | Cleary | 119/96 X |
| 2,910,980 | 11/1959 | Stewart | 128/152 |
| 3,257,990 | 6/1966 | Robertson et al. | 119/96 |
| 3,603,309 | 9/1971 | Wesemann | 128/152 |
| 3,833,701 | 9/1974 | Johnson et al. | 128/152 X |

*Primary Examiner*—John D. Yasko
*Attorney, Agent, or Firm*—Schmidt, Johnson, Hovey & Williams

[57] ABSTRACT

The ear of an animal is supported as it heals by a soft, pliable body that conforms to the interior surface of the ear and is attached thereto until healed by such means as adhesive tape, suturing, adhesive between the interior ear surface and the body, or any combination thereof. The flap-like outer portion of the body lies against the pinna of the ear and can flex with the ear as need be, while the inner stem portion of the body projects partially into the ear canal and is of somewhat greater rigor than the flap portion so as to promote retention of the pinna in a generally erect condition.

8 Claims, 7 Drawing Figures

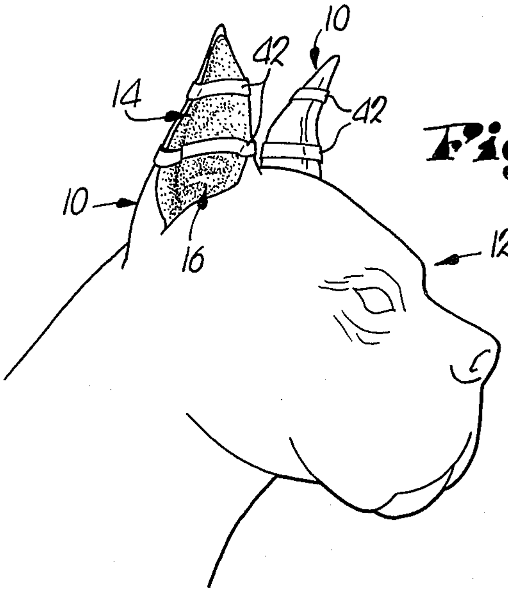
Fig. 1.
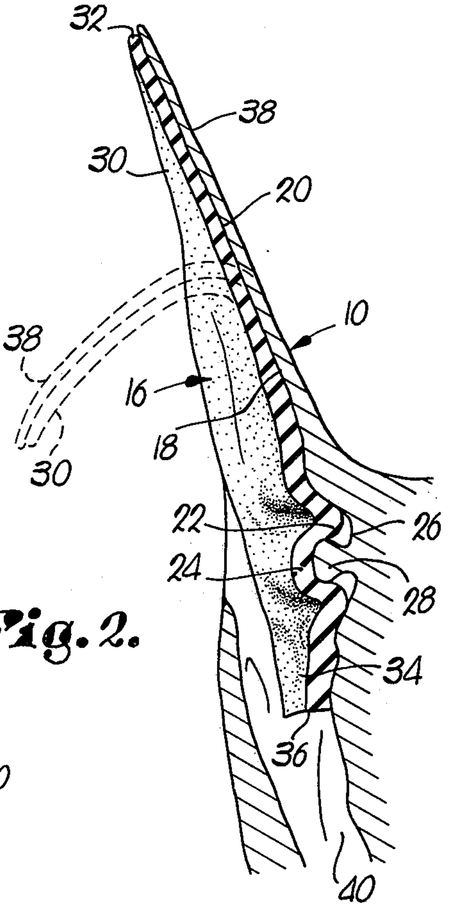
Fig. 2.
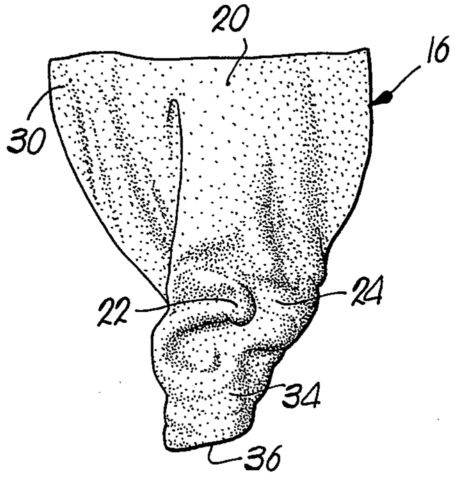
Fig. 3.
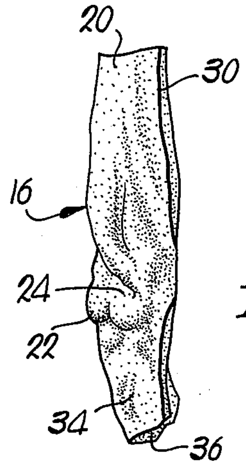
Fig. 4.
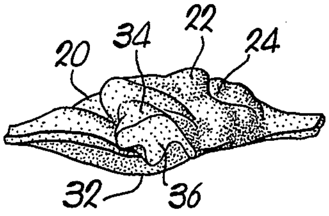
Fig. 5.
Fig. 6.
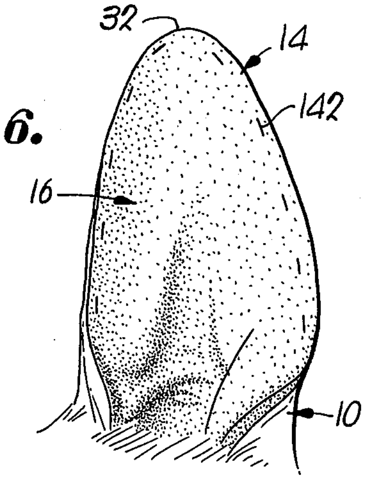
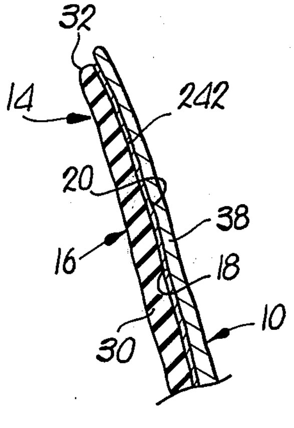
Fig. 7.

ANIMAL EAR SUPPORT DEVICE

This invention relates to the treatment of animals' ears such as after cosmetic surgery to trim the ears, or such as during the period that the ears are healing following traumatic injuries. More particularly, it relates to supporting an ear in need of healing by attaching a soft, pliable, self-supporting body that conforms substantially to the interior surface of the ear against such interior surface to yieldably hold the ear in a generally erect condition until the ear has sufficiently healed to support itself.

While the general concept of holding the ears of a dog or other animal in an erect condition following cosmetic surgery to trim the ears for appearance purposes or for holding them in such condition after traumatic injury is not new per se, prior devices of which I am aware have included awkward structures in the nature of wire frames placed on the animal's head and attached to the outside of the ears. Such an arrangement is highly undesirable for a number of reasons, not the least of which is the fact that such frames are difficult to keep in place and may cause serious injury when the animal shakes his head violently or rubs it against other objects in an effort to be rid of the irritating adornment.

Therefore, it is one important object of the present invention to provide an animal ear support having a body that fits neatly into and lies against the interior surface of the animal's ear so as to hold the ear in a generally erect condition, without the use of exterior metal frames and the like, until damaged or surgically weakened cartilage in the ear can regain its normal strength and rigidity to support the ear on its own.

Another important object of this invention is to provide a support as above-described wherein its body is stiff enough to provide the required degree of support for the healing ear and yet is sufficiently soft and pliable to flex with the ear under certain conditions so as to remain in place and prevent bruising of the ear should it be brushed against solid objects.

Another important object of this invention is the provision of a support as aforesaid which may be readily provided in a number of assorted sizes to accommodate various breeds of dogs, for example, and which is sufficiently inexpensive to fabricate that it can be disposed of after each use.

An additional important object is to provide an ear support which is readily adapted to be trimmed in certain areas as may be required to properly fit the animal's ear without extending outwardly beyond its edges.

A still further important object of the present invention is the provision of supporting body that can be readily attached and detached from an animal's ear such as by adhesive tape, suturing, and adhesive between the body and the ear, or any combination thereof.

In the drawing:

FIG. 1 is a perspective view of a dog's head showing the support of the present invention attached to the ears of the dog;

FIG. 2 is an enlarged, fragmentary, vertical cross-sectional view through the head showing the manner in which the body of the ear support conforms closely to the interior surface of the ear and illustrating in phantom the manner in which the body can flex with the ear;

FIG. 3 is an enlarged, fragmentary elevational view of the lower back of the body;

FIG. 4 is a side elevational view of such lower portion;

FIG. 5 is a bottom view of the body;

FIG. 6 is a view of the body in place, illustrating attachment to the ear by suturing; and FIG. 7 is a cross-sectional view of the body in place using adhesive to attach the body to the ear.

The ear support of the present invention may be used on any type of animal, since it may be molded to conform to the shape of any ear, but for purposes of illustration, the support is shown in conjunction with the ears 10 of a dog 12 in FIG. 1. The support 14 is fully visible on the right ear 10 of the dog 12, but its counterpart on the left ear 10 is substantially hidden from view. It is to be understood that the supports 14 for the two ears 10 are mirror images of one another, but in all other respects are substantially identical. Therefore, the description which follows is of one support 14.

Support 14 includes an elongated, soft, pliable body 16 of generally concavo-convex configuration which conforms substantially to the interior surface 18 of ear 10. The convex side 20 of body 16 lies against interior surface 18 when support 14 is in use, and such convex side 20 has numerous ridges and valleys such as at 22 and 24 respectively that are generally complemental to corresponding valleys and ridges 26 and 28 respectively in the ear 10. Such an arrangement helps to maintain the body 16 securely in place, in addition to other means not yet described, when the support 14 is in use for treatment. It should be noted that valleys 24 in convex side 20 are wider mouthed than the peaks of ridges 28 in ear 10 so as to facilitate reception of ridges 28 into valleys 24 during insertion of support 10.

Body 16 also has a flap-like outer portion 30 extending from the tip 32 of body 16 downwardly to approximately three-quarters the overall length of body 16 whereupon a more rigid, narrower stem portion 34 commences which extends to the lower end 36 of the body 16. As illustrated best in FIG. 2, the flap portion 30 lies primarily against the corresponding flap-like portion or pinna 38 of ear 10, while the stem portion 34 projects into the ear canal 40.

Body 16 may be made from any non-toxic, non-irritating, light, pliable material such as, for example, silicone rubber, and while it is desirable for the body 16 to be flexible, at the same time it must be self-supporting and have sufficient strength to provide a degree of support for the ear 10. In this regard, flap portion 30 may most easily bend with the pinna 38 of ear 10 as shown in fantom in FIG. 2, while the stem portion 34, through its increased rigor due to the concentration of ridges 22 and valleys 24, resists bending and hence promotes retention of the flap portion 30 and pinna 38 in a generally erect condition.

The support 14 also includes means for removably attaching the body 16 to ear 10. Such attaching means may take several different forms, as well as a combination of different forms, and in FIG. 1 the attaching means takes the form of adhesive tape denoted by the numeral 42. As illustrated, such tape 42 is preferably wrapped fully about both the body 16 and the ear 10 at two or more vertically spaced locations in order to fully secure body 16 in place.

FIG. 6 illustrates a different manner of attaching the body 16 to the ear 10, such taking the form of sutures 142 about the periphery of body 16. After healing, sutures 142 can, of course, be readily removed, and it is to be understood that in some circumstances it may be desirable to use not only sutures 142, but also adhesive tape 42.

FIG. 7 shows yet another alternative means of detachably securing the body 16 to ear 10, and this form utilizes an adhesive layer 242 applied between the convex side 20 of body 16 and the interior surface 18 of ear 10. Although many different types of adhesive 242 might be appropriate, it has been found that "Vi-Drape" adhesive sold by Parke, Davis & Company has been satisfactory. Another suitable product is "Silastic Medical Adhesive, Silicone-Type A" sold by Dow Corning Corporation.

Vi-Drape adhesive contains co-polymers of hydroxyvinyl chloride-acetate and sebacic acid, 7.5% by weight, modified maleic rosin estev, 1.9% by weight, and glycolate plasticizer, 3.1% by weight, in an ethyl acetate-acetone solvent with fluorochloro hydrocarbon as a gaseous propellant. The Silastic Medical Adhesive is silicone-type A as above-mentioned.

The Vi-Drape adhesive is probably more suitable for an animal that will wake up in a short period of time because it cures more rapidly than the Silastic Medical Adhesive. Either type, however, will give adequate adhesion if the animal is maintained under sedation for several hours. In some instances, it may even be desirable to use the adhesive tape 42 in addition to the adhesive layer 242, and this combination provides a very secure means of attaching the body 16 to the ear 10. In this respect, it has been found that body 16 is retained in place even during violent shaking of the dog's head and frequent pawing at the ear.

It is contemplated that instead of preparing a new body 16 for each dog, several different sizes will be prepared and stocked corresponding to different breeds and sizes of dogs. Because the flap portion 30 of body 16 need not cover the entire interior surface 18 of ear 10, it is possible to utilize a slightly smaller-than-illustrated body 16 in certain circumstances. On the other hand, the nature of body 16 adapts the latter to be readily trimmed as need be to fit smaller sizes of ears, and this flexibility of design enables the veterinarian to keep a considerably smaller volume of each size bodies on hand.

The bodies 16 may be produced through a relatively simple molding process which involves making a plaster of Paris casting of the ear 10, producing a mold, and pouring liquid silicone rubber or other suitable substance into the mold in a conventional manner to produce the body 16. After the plaster of Paris casting has been made and before production of the mold, the mouths of valleys in the casting are widened so they are no longer precisely complemental to ridges 28 within ear 10. Since such ridges 28 have enlarged or bulb-like outermost extremities, the valleys 24 on support 14 that will ultimately receive ridges 28 must be wide enough at their mouths to permit ready entry of the bulbed extremities during the time that support 14 is being inserted into the ear 10. Hence, the casting is altered prior to production of the mold. As is apparent, the bodies 16 may be produced in any quantity so that the veterinarian will have a sufficient number on hand to satisfy his needs.

It will be appreciated from the foregoing that the ear support 14 of the present invention provides a significant improvement over known prior ear supports, such as, for example, the head-mounted frame-type supports which attach to the outside surfaces of the animals' ears. The soft, pliable body 16 of each support 14 is non-irritating to the animal in contrast to such rigid frames, and its softness and pliability help to not only maintain body 16 adhered to the ear 10, but also help to preclude any injury to the ear 10 as a result of having the support 14 placed thereon. In these regards, if body 16 were rigid and unyielding, it is quite likely that it would be unable to withstand the terrific centrifugal forces which are generated when an animal shakes his head violently, thus causing the body 16 to become detached from the ear under such circumstances. Moreover, if body 16 were unyielding, such could quite possibly lead to serious bruising or mutilating of the ear should the dog brush up against solid objects or paw aggressively at his ear.

The support 14 can, of course, be of considerable assistance in a number of different situations. One example of such usage is where the dog's ears have been trimmed for cosmetic purposes. Following such minor surgery, it is necessary to maintain the ears in a substantially erect condition until such time as the cartilage has strengthened sufficiently that it can hold the ears in an erect condition without assistance of some external support. Another situation arises where the dog may have been involved in altercations with another dog resulting in ear damage. It may be necessary in that situation to support the ear firmly while the ear tissue and cartilage heal and medication is applied. Moreover, in such situations of traumatic injury to the ear, it may be necessary for the veterinarian to perform surgery, in which event, cartilage may be weakened, requiring fairly prolonged support from an external source.

It should also be apparent that the relatively noncomplex nature of the ear support 14 of the present invention allows the same to be produced rather economically such that it may be considered a disposable item. Hence, the body 16 need not be sanitized after use, but can simply be discarded. On the other hand, the body 16 could be prepared for additional uses by sanitizing the same in an autoclave or the like.

It should be noted also that as shown in FIG. 2, the stem 34 of body 16 does not occupy the entire cross-sectional area of the ear canal 40. Hence, canal 40 can receive a sufficient flow of fresh air to keep the same and the adjacent areas of the ear well aerated.

Use of the support 14 need not be limited solely to aiding in the healing of an animal's ear. In this respect the veterinarian may find it helpful during cosmetic surgery itself, rather than simply using the support to promote healing after surgery has been completed. By first placing support 14 in the ear to be trimmed and then cutting support 14 around its edges as need be to conform to the shape of the pinna, the veterinarian has an accurate replica of the ear. He may then cut the support 14 to assume the desired cosmetic appearance, reinsert it into the ear using one or more of the attachment methods specified above, and trim away the overlapping pinna portions. This enables the veterinarian to have a preview of the way the trimmed ear will appear once surgery has been completed and, further, assures that both ears of an animal will be identically trimmed if both supports are first identically shaped.

Having thus described the invention, what is claimed as new and desired to be secured by letters patent is:

1. An animal ear support comprising a pliable, self-supporting, generally concavo-convex body conforming substantially to the interior surface of the animal ear with which the support is to be used, and means for removably attaching said body to the ear against said interior surface, said body including an outer flap portion adapted to bend with the ear and an inner stem portion of increased rigor relative to the flap portion adapted to fit at least partially into the ear canal to promote retention of the ear and flap portion in an erect condition.

2. An animal ear support as claimed in claim 1, wherein said attaching means includes adhesive tape.

3. An animal ear support as claimed in claim 1, wherein said attaching means includes a suture between the body and the ear.

4. An animal ear support as claimed in claim 1, wherein said attaching means includes an adhesive layer between the body and said interior surface.

5. A method of treating an animal having an ear in need of healing, said method including the steps of attaching a flexible, self-supporting body which conforms to the interior surface of the ear against said interior surface; supporting the ear with said body until healed, said body including an outer flap portion adapted to bend with the ear and an inner stem portion of increased rigor relative to the flap portion fitting at least partially into the ear canal to promote retention of the ear and flap portion in an erect condition, and detaching the body from said interior surface after the ear has healed.

6. A treating method as claimed in claim 5, wherein said attaching step includes applying adhesive tape to the body and ear.

7. A treating method as claimed in claim 5, wherein said attaching step includes suturing the body to the ear.

8. A treating method as claimed in claim 5, wherein said attaching step includes applying an adhesive between the body and said interior surface of the ear.

* * * * *